United States Patent [19]
Lonchamp et al.

[11] Patent Number: 5,470,370
[45] Date of Patent: Nov. 28, 1995

[54] COMPLEX COMPOSITION RESULTING FROM THE ACTION OF UREA ON A SULFURIC SLUDGE OF PETROLEUM ORIGIN, PROCESS FOR THE PREPARATION THEREOF AND USE THEREOF AS A SOURCE OF FERTILIZING MATERIAL

[75] Inventors: Daniel Lonchamp, Tassin La Demi Lune; Yvan Schwob, Cannes, both of France

[73] Assignees: Institut Francais Du Petrole, Rueil Malmaison; Transvalor, Paris, both of France

[21] Appl. No.: 267,694

[22] Filed: Jun. 29, 1994

[30] Foreign Application Priority Data

Jun. 29, 1993 [FR] France ............................ 93/08.044

[51] Int. Cl.$^6$ .............................. C05C 9/00; C05F 7/00; C07C 273/02
[52] U.S. Cl. ...................................... 71/25; 71/28; 564/63
[58] Field of Search ............................ 71/25, 28; 564/63

[56] References Cited

U.S. PATENT DOCUMENTS

| 4,397,675 | 8/1983 | Young | 71/28 |
| 4,436,545 | 3/1984 | Lyons, Jr. et al. | 71/25 |
| 4,447,253 | 5/1984 | Young | 71/28 |
| 4,944,787 | 7/1990 | Young | 71/28 |
| 4,962,283 | 10/1990 | Harbolt et al. | 71/28 |

FOREIGN PATENT DOCUMENTS

| 0041488 | 12/1981 | European Pat. Off. . |
| 0345948 | 12/1989 | European Pat. Off. . |

OTHER PUBLICATIONS

Chemical Abstracts, vol. 113, No. 18, Oct. 29, 1990, Abstract No. 155239k (abstract of CS-A-262,211).

Primary Examiner—Wayne Langel
Attorney, Agent, or Firm—Millen, White, Zelano & Branigan

[57] ABSTRACT

A complex composition formed by the product resulting from the action of urea on a sludge of petroleum origin containing by weight from 50 to 99% of sulfuric acid and from 1 to 20% of organic residues. The acid sludge may contain water and often comes from an alkylation reaction. This composition can be used as a source of fertilizing material or as a component of a fertilizing formulation.

5 Claims, 1 Drawing Sheet

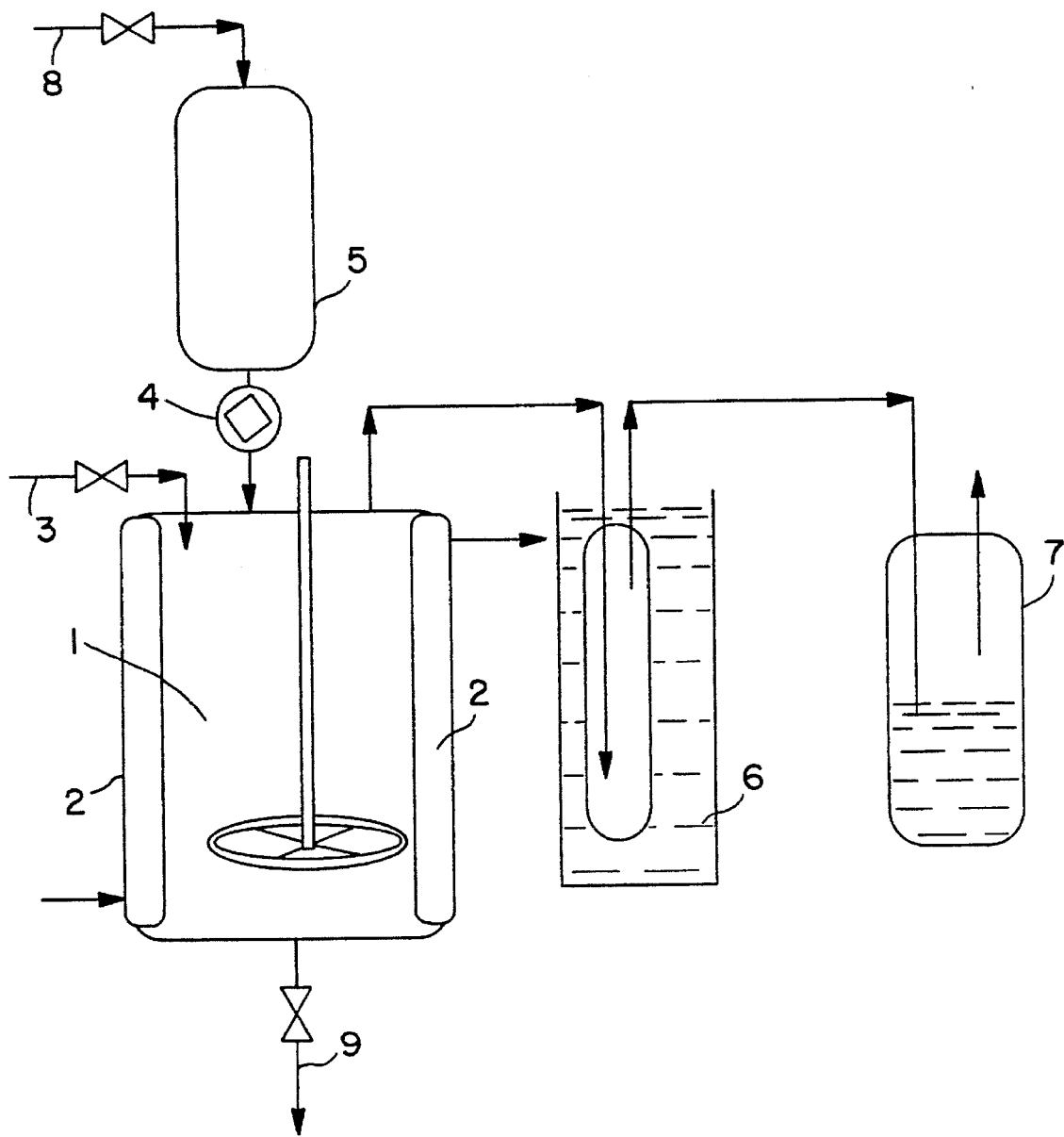

COMPLEX COMPOSITION RESULTING FROM THE ACTION OF UREA ON A SULFURIC SLUDGE OF PETROLEUM ORIGIN, PROCESS FOR THE PREPARATION THEREOF AND USE THEREOF AS A SOURCE OF FERTILIZING MATERIAL

BACKGROUND OF THE INVENTION

The present invention concerns a process for treating and imparting value to sulfuric sludges of petroleum origin which essentially consists of reacting said sludges on urea in defined proportions in such a way as to involve the sulfuric acid in a particular sulfuric acid urea complex composition. It also concerns the composition resulting from said process. The process makes it possible to recover sulfuric acid in order to impart value thereto as well as a part of the organic compounds present in the sludges.

The prior art is illustrated in particular by U.S. Pat. No. 4,397,675 and by the article Chem. Abstracts, Vol 113, No 18, 29th October 1990, Columbus, Ohio, U.S.; Abstract No 155 239 k, page 166.

It is known that certain chemical operations, in particular those which are effected in alkylation procedures, and in particular aliphatic alkylation procedures, are carried out in the presence of concentrated sulfuric acid which performs a catalysis function. Unfortunately a part of the acid involved occurs at the end of the operation in the form of impure sulfuric sludges, the elimination of which gives rise to many problems. The present invention makes it possible in particular to treat and impart value to such sludges which result from aliphatic alkylation reactions.

The man skilled in the art knows that the essential part of such sludges is formed by mixtures or complex combinations as between sulfuric acid and certain organic residues. Their mean composition by weight fluctuates between the following values, expressed as a percentage by weight:

$H_2SO_4$ 88 to 96%

$H_2O$ 2 to 6% organic residues 2 to 6%.

The applicants found that treatment of such sludges by means of urea in a defined proportion could give rise to compositions which can be put to valuable use while a part of the organic residues, for example in the form of hydrocarbons, could also be recovered.

It is known to obtain, as between urea and sulfuric acid, mono- and bi-urea complexes with well-defined melting points. It is also known that the complexes, as between themselves and with urea, give compounds which are fusible at low temperature. Thus a eutectic comprising 3.6 moles of urea for one mole of sulfuric acid occurs in the form of a liquid which is stable at a temperature close to 25° C.

SUMMARY OF THE INVENTION

The applicants surprisingly found that impure sulfuric acid resulting from alkylation operations could also permit the production of such combinations and that the excess of urea used for that purpose resulted in such combinations and in addition that such excess resulted in the liberation, by a kind of saponification effect, of a part of the organic compounds which were previously blocked by the acid. The sulfuric sludges can be considered as being a mixture of acid, water and acid sulfate of hydrocarbons and in particular alkyl acid sulfate. If we use R to designate the organic residue or residues which are bonded to the acid, the mixture can be considered as follows:

$$aSO_4 H_2 - bSO_4 HR - cH_2O$$

in which a, b and c represent the number of moles of each compound present in the mixture. It is also known that the presence of a small amount of water in that compound can be accepted without giving rise to any particular problem.

Surprisingly the action of urea on the sulfuric acid contained in those acid sludges takes place as in the conventional process for producing a thiourea compound, as is the case with substantially pure sulfuric acid. The action of the urea in excess on the acid sulfates of hydrocarbons results in a kind of saponification effect in the presence of water and which can be written as follows for example in the case of alkyl acid sulfate:

$$SO_4HR + 2CO(NH_2)_2 + H_2O \rightarrow SO_4H_2 2CO(NH_2)_2 + R-OH$$

Depending on the molecular weight of R and the operating conditions (temperature and pressure), the compounds R—OH can be recovered.

More precisely the invention concerns a thiourea composition which is the product resulting from the action of urea on a sulfuric sludge of petroleum origin containing by weight from 50 to 99% of sulfuric acid and from 1 to 20% of organic residues. In most cases the organic sludge of petroleum origin also contains water in an amount representing up to 6% by weight with respect to the total weight of the sludge. In most cases the sulfuric sludge of petroleum origin contains from 70% to 98% by weight of sulfuric acid and from 2 to 10% of organic residues.

The residual sulfuric sludge is firstly chemically analysed so as precisely to ascertain its contents of water, organic materials and sulfuric acid. The latter is determined by any known means, so as to obtain the proportion of total acidity contained in the sludge. A simple method in this respect comprises for example reacting an aliquot part of sludge with an excess of a strong base such as for example sodium hydroxide and in return quantitatively ascertaining the excess remaining after neutralization of the sludge. By virtue of the use of titrated solutions it is easy thus to ascertain the total amount of sulfuric acid present. The amount of water contained in the sludge can be determined for example by means of the conventional method referred to as the Karl-Fischer method.

That calculation having been carried out the sludge is reacted with an amount of urea such that the molar ratio between the urea and the total acid contained in the sludge (as ascertained by the quantitative measuring operation) is for example about 1:1 to about 4:1 and preferably about 3:1 to about 4:1.

In a particular embodiment of the present invention the amount of water contained in the sludge can if necessary be adjusted by the addition of water to the sludge in such a way that the molar ratio as between the water and the total acid is about 1:1 to about 6:1 and preferably about 1:1 to about 4:1. That amount of water can be adjusted in dependence on the use involved and transportation in the liquid or solid phase of the composition.

The reaction of urea on the sludge being strongly exothermic it is appropriate to use any known means for removing the excessive heat so as preferably to limit the maximum temperature of the medium in the course of the reaction to 75°, subject otherwise to seeing a part of the urea suffer from decomposition it ion due to the Kjeldahl effect to form ammonium sulfate.

It is thus possible to operate in a discontinuous or a continuous mode. When operation is effected in a continuous mode, it is preferable to introduce the reactants, that is to say the sludge, urea and if necessary water, in a mixture which is referred to as a sulfuric acid-urea complex mixture and which is obtained in a preceding discontinuous reaction.

The use of solid urea affords the advantage of furnishing in the reaction medium the negative heat of solution which is practically equal to the heat of fusion. In that way the risk of an abnormal increase in temperature is greatly limited and temperature control is facilitated.

When those operations are carried out at temperatures of between about 20° C. and 75° C. and at atmospheric pressure, gas is seen to be given off. That gas contains sulfurous anhydride which can be recovered by any means known to the man skilled in the art.

The compositions which are obtained in that way, titrating between 15 and 31% by weight of nitrogen, can be usefully employed as a source of fertilizing material, either alone or after mixing in combination with other fertilizing elements. The process of the invention thus makes it possible to impart value to acid sludges and to avoid the need for the expensive operation of eliminating same. The present invention also concerns the use of the compositions described hereinbefore as a component of a fertilizing formulation.

BRIEF DESCRIPTION OF THE DRAWING

Various other objects, features and attendant advantages of the present invention will be more fully appreciated as the same becomes better understood when considered in conjunction with the acompanying drawing which depicts a schematic embodiment of an apparatus which is employed to conduct the process of the invention.

Example 1

A sludge issuing from a sulfuric alkylation unit is of the following composition expressed as a percentage by weight:

sulfuric acid 90.2 water 4.7 hydrocarbons 5.1.

1000 (g) grams of that alkylation sludge is poured into an agitated reactor (1) maintained at a constant temperature of 40° C. by external temperature control means (2) (see the accompanying FIGURE).

117 g of water is added slowly by way of the conduit (3), then a part of the urea contained in the reservoir (5) is added by means of the gate valve (4).

The addition of urea is firstly effected slowly to prevent any rise in temperature, that is to say the rate of addition is regulated by increments to keep the temperature constant at 40° C., and then more rapidly when the amount of urea added corresponds to the formation of the mono-urea complex, that is to say after the addition of about 600 g of urea.

In total 1988 g of commercial granulated urea is added. Those amounts are such that the urea: water: acid molar proportions are 3.6:1:1. The gases which are given off are firstly cooled in the trap (6) which is maintained at a temperature of −40° C. and then bubble into the trap (7) which contains a 10% by volume solution of hydrogen peroxide.

When the urea has been entirely introduced into the reactor (1) the whole of the apparatus is purged by the introduction of a slight flow of air by way of the conduit (3). In that way the sulfurous anhydride which may still be contained in the reactor (1), in the conduits and in the trap (6) is displaced towards the trap (7) in which the sulfurous anhydride is converted into sulfuric acid. Quantitative analysis of that acid makes it possible to ascertain the amount of sulfurous anhydride given off. That amount is 0.91 g.

The resultant complex formed in the reactor is a dark brown liquid which is recovered by way of the conduit (9) and which is left to settle for several hours at ambient temperature. Its content by weight of nitrogen is 30.3%. There appears at the surface a thin film of a black product of tarry appearance which hardens by cooling. That product can be recovered by being skimmed off. It represents 45 g.

Example 2

This Example involves preparing a complex which, as in Example 1, has a urea/$H_2SO_4$ molar ratio of 3.6, but with a crystallization temperature of the order of −10° C. The alkylation sludge is that used in Example 1.

The reactor is maintained at 25° C. by external temperature control. 537 g of water is added slowly with strong agitation to prevent any excessive rise in temperature.

Then, as in Example 1, 1988 g of technical granulated urea is added until complete dissolution has occurred. Those amounts are such that the urea: water: acid molar proportions are 3.6:3.5:1.

At ambient temperature the complex formed contains 26.3% by weight of nitrogen and leaves to settle a blackish film of hydrocarbons which can be removed by being skimmed off and which represents 44 g.

Example 3

Another sludge resulting from sulfuric alkylation is of the following composition expressed as a percentage by weight:

sulfuric acid 95.2 water 2.8 hydrocarbons 2.0.

Taking the reactor described in Example 1 1000 g of that sulfuric sludge is poured into the reactor and 147 g of water is added slowly with strong agitation.

The reactor is thermostatically controlled at 50° C. 2097 g of granulated urea is then added in a period of about 30 minutes. Those amounts are such that the urea: water: acid molar proportions at 3.6:1:1.

The sulfuric acid for in the trap (7) containing 10% by volume hydrogen peroxide corresponds to 0.1 g of sulfurous anhydride.

The liquid complex is left at rest for 2 hours at 50° C. and then for one night at ambient temperature. A very thin layer of semi-solid hydrocarbons is formed at the surface and can be easily removed. Its weight is 18.8 g. The proportion by weight of nitrogen in the composition after the skimming operation is 30%.

Example 4

Using the alkylation sludge of Example 3, this Example involves forming a complex which is liquid at ambient temperature but in which the urea/sulfuric acid molar ratio is 1.2. The amounts are such that the urea: water: acid molar proportions are 1.2:1.4:1.

The reactor is maintained at 25° C. and 217 g of water and 700 g of granulated urea are added to 1000 g of alkylation sludge.

The liquid complex is left at rest for 2 hours at 50° C. and then for one night at ambient temperature. Its nitrogen content is 17.2%. A very thin layer of semi-solid hydrocarbons is formed at the surface and can be easily removed. Its weight is 16.7 g.

We claim:

1. A process for the preparation of a fertilizer composition comprising reacting at a temperature which is at most equal to 75° C. urea, a sulfuric sludge from an aliphatic alkylation reaction containing by weight 50 to 99% of sulfuric acid and 1 to 20% of organic residue and water, in an amount such that the molar ratio between the urea and the total acid contained in the sludge is from about 1:1 to about 4:1 and the molar ratio between the water and the total acid contained in the sludge is from about 1:1 to about 6:1, to form a liquid phase containing a sulfuric acid-urea complex and above the liquid phase a semi-solid hydrocarbon film; decanting the film from the solution obtained and recovering the fertilizer composition.

2. A process according to claim 1, wherein the action of the urea on the sulfuric sludge is effected while limiting the temperature of the medium to a value which is at most equal to about 75° C.

3. A process according to claim 1, wherein the action of the urea on the sulfuric sludge is effected under atmospheric pressure and at a temperature of from about 20° C. to about 75° C.

4. A process according to claim 1, wherein the urea/$H_2SO_4$ molar ratio is 3.6:1.

5. The process according to claim 1, wherein the urea/$H_2SO_4$ molar ratio is 1.2:1.

* * * * *